United States Patent [19]

Ahlstrom, Jr. et al.

[11] 4,272,481
[45] Jun. 9, 1981

[54] SYSTEM AND METHOD FOR PROVIDING A VAPOR PHASE SAMPLE FOR ANALYSIS

[75] Inventors: Ross C. Ahlstrom, Jr., Lake Jackson; Craig E. Meppen, New Braunfels, both of Tex.

[73] Assignee: The Dow Chemical Company, Midland, Mich.

[21] Appl. No.: 41,158

[22] Filed: May 21, 1979

[51] Int. Cl.$^3$ .............. G01N 21/00; G01N 7/00; G01N 31/08
[52] U.S. Cl. .............................. 422/62; 422/83; 422/101; 23/230 A
[58] Field of Search ............ 422/89, 83, 62, 106, 422/101, 81, 80; 23/230 M, 232 C, 232 R, 232 E, 230 A, 230 PC; 173/23, 23.1; 134/22 C, 37

[56] References Cited

U.S. PATENT DOCUMENTS

| | | | |
|---|---|---|---|
| 2,289,351 | 7/1942 | Dixon et al. | 134/22 C |
| 3,002,372 | 10/1961 | Bulkley et al. | 422/83 |
| 3,285,701 | 11/1966 | Robertson | 422/89 |
| 3,424,557 | 1/1969 | Skeggs | 422/81 |
| 3,641,821 | 2/1972 | Neubeyer et al. | 422/83 |
| 3,690,833 | 9/1972 | Ferrari | 422/81 |
| 3,897,211 | 7/1975 | Ririe | 422/89 |
| 4,095,951 | 6/1978 | Dicola et al. | 422/80 |

FOREIGN PATENT DOCUMENTS 2410824  6/1979  France .................................. 422/81

Primary Examiner—William F. Smith
Assistant Examiner—Chris Konkol
Attorney, Agent, or Firm—V. Dean Clausen

[57] ABSTRACT

The present sampling system provides a means for continuous vapor phase analysis of an indefinite number of process streams in a single operation. The process being sampled is connected into a single analyzing instrument by more than one delivery conduit. Each delivery conduit is heated between the process and the analyzer to a temperature sufficient to maintain the selected sample in its vapor state. During the sampling only one delivery conduit is carrying the sample into the analyzer. At the same time, a purge fluid is being backflushed into the process through each remaining delivery conduit. The backflushing sequence clears out polymerizable materials or other substances which tend to collect inside the conduit.

5 Claims, 1 Drawing Figure

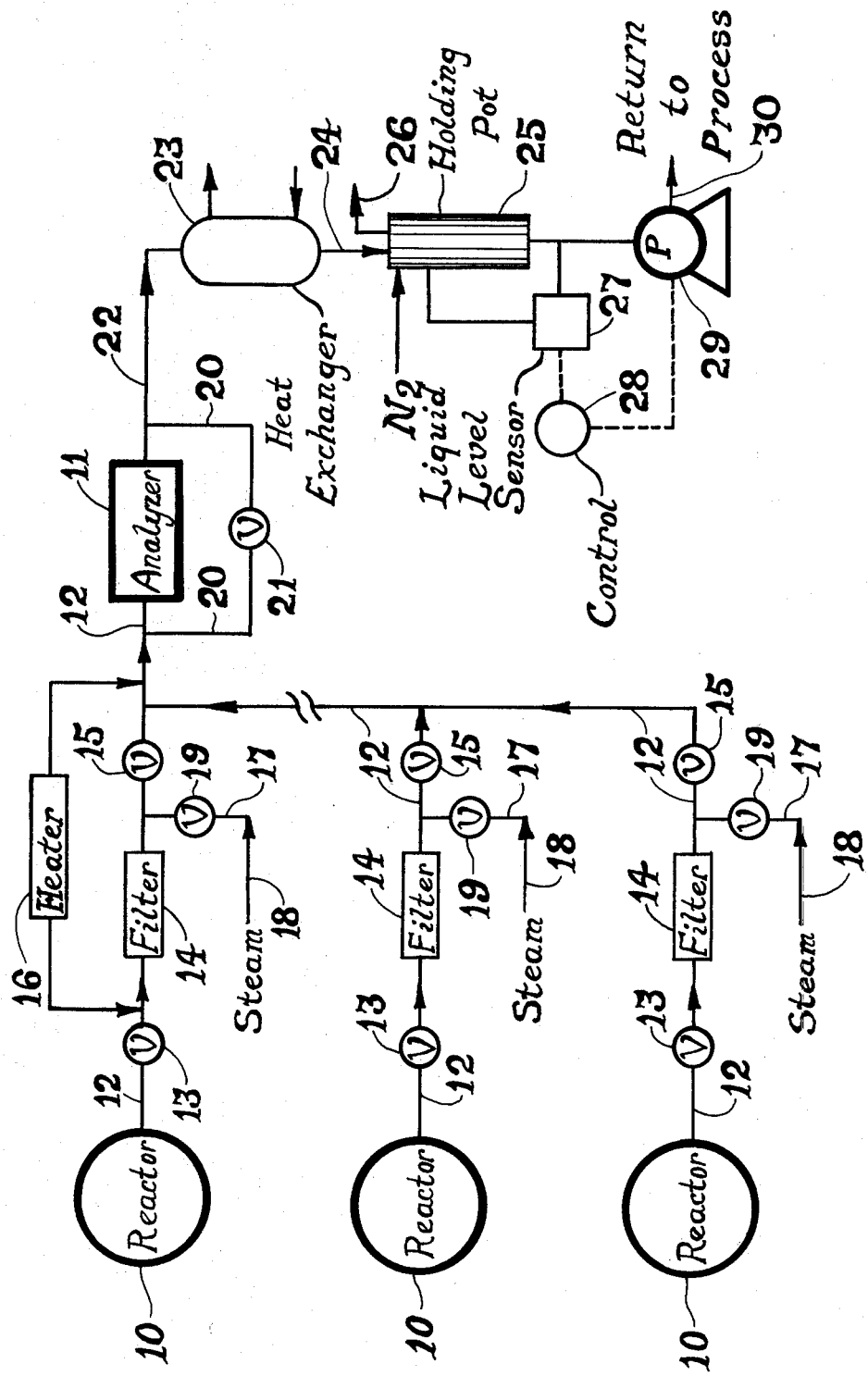

SYSTEM AND METHOD FOR PROVIDING A VAPOR PHASE SAMPLE FOR ANALYSIS

BACKGROUND OF THE INVENTION

Broadly, the invention relates to providing a vapor phase sample for analysis. More specifically, the invention is directed to providing a vapor phase sample for analysis, in which the sample, at ambient temperature and pressure, contains a mixture of condensable and non-condensable components.

In some chemical processes the composition of the product, at ambient temperature and pressure, is a mixture of a non-condensable gas phase, an aqueous phase, and an organic liquid phase. An example of such a product is a mixture which contains, water, hydrogen, oxides of carbon, aromatic hydrocarbons, and aliphatic hydrocarbons. It is very difficult to achieve reliable on-line sampling of such a mixture, particularly if the aromatic hydrocarbons are polymerizable materials. For example, in certain types of sampling systems the polymer materials will build up in the sampling line and plug it off entirely.

There are several other problems in the on-line sampling of such a composition. For example, in one of the prior sampling techniques the sample mixture described above is collected from the chemical process and thereafter cooled. The cooling step condenses the water, the aromatic hydrocarbons, and some of the aliphatic hydrocarbons. The water and the organic liquid phases are then analyzed separately. However, it is extremely difficult to analyze the non-condensable gas phase, because some of the water and the hydrocarbons become entrained in the non-condensable gas phase.

The present invention eliminates the problems described above in that it provides a system in which the entire sample mixture is delivered to an on-line analyzer as a vapor phase sample.

DESCRIPTION OF THE DRAWINGS

The single FIGURE is a schematic illustration of one embodiment of the vapor phase sampling system of this invention.

SUMMARY OF THE INVENTION

The sampling system of this invention includes an analyzer means adapted for receiving and analyzing a vapor phase sample. The analyzer is connected by at least one delivery conduit to a chemical process apparatus, which provides means for delivering the vapor phase sample to the analyzer. The sample, as taken from the process apparatus, is in a vapor phase. A heater means associated with each delivery conduit heats each conduit to a temperature sufficient to maintain the sample in a vapor state. A shut-off valve and a stream select valve are also installed in each delivery conduit between the process apparatus and the analyzer.

The shut-off valve isolates the sampling system from the process apparatus and the stream select valve selects a specific portion of the vapor phase sample to be delivered to the analyzer. A purge conduit is connected into each of the delivery conduits ahead of the stream select valve and behind (downstream) the shut-off valve. This conduit carries a purge fluid, which is compatible with the chemical process involved, into the delivery conduit, and a backflush valve installed in the purge conduit forces the purge fluid back into the process apparatus. Connected into the analyzer means is a suitable discharge means for carrying the vapor phase sample out of the analyzer.

DESCRIPTION OF A PREFERRED EMBODIMENT

Referring to the drawing, the numeral 10 indicates a conventional chemical process apparatus, for example, a reactor. In practice, a sample of the chemical product in the process is periodically removed from the reactor 10 (or other apparatus), for analysis in an on-line analyzer 11. Referring specifically to the top part of the drawing, there is shown a delivery conduit 12 which connects the reactor 10 into the analyzer 11. Installed in the delivery conduit 12 (downstream from the reactor) is a shut-off valve 13, a filter unit 14, and a stream select valve 15.

The delivery conduit 12 provides a means for delivering the sample from reactor 10 into analyzer 11. Shut-off valve 13 is a means for isolating the sampling system from the reactor 10. In some analyzing procedures it may be desirable to remove particulate matter from the sample before it is injected into the analyzer 11. This function is performed by the filter unit 14. In other situations the chemical material to be analyzed may not include entrained particulate matter. When this is the case, there is no need to include a filter unit in the sampling system.

In the embodiment of the sampling system described and illustrated herein the chemical material to be analyzed is a vapor phase product at the time it leaves the process apparatus, such as reactor 10. To overcome the problems mentioned earlier, the chemical sample is maintained in its vapor phase and thereafter analyzed as a vapor phase sample. The delivery conduit 12 is heated between valve 13 and analyzer 11, by a heater means 16, to a temperature high enough to maintain the vapor state. The heater means 16 can be a suitable conventional heating device, such as a steam trace line.

A purge conduit 17 is connected into the delivery conduit 12 ahead of the stream select valve 15. As indicated in the drawing, a purge fluid, such as steam, is directed into conduit 17 from a suitable source, such as a steam line 18. Installed in conduit 17 is a backflush valve 19.

At a given point in the sampling operation the stream select valve 15 is deactivated to stop flow of the sample into the analyzer 11. At the same time, the backflush valve 19 is activated, to backflush the purge fluid through the delivery conduit 12 and back into the process apparatus (reactor 10). The backflushing sequence cleans the delivery conduit of any polymerizable materials, or other substances, that may tend to collect in the conduit during the sampling sequence.

OPERATION

In a typical operation of the present sampling system the analyzer 11 can be connected into any number of reactors, or other types of chemical process apparatus. This feature of the invention permits the continuous vapor phase analysis of an indefinite number of process streams in a single operation. In actual practice the number of process streams which can be tied into the (one) analyzer 11 will depend on the specific requirements of the chemical process which is being sampled. For example, as shown in the drawing, there are three reactors tied into the (one) analyzer 11 (each reactor being indicated by the numeral 10). Specifically, each of the reactors 10 is connected into the analyzer 11 by a delivery conduit 12. Each of the delivery conduits 12 includes a shut-off valve 13 and a stream select valve 15.

As mentioned earlier, a filter unit 14 can be installed in each of the delivery conduits 12 in those situations which require removal of particulate matter from the vapor phase sample prior to injection into the analyzer 11. A purge conduit 17 is also connected into each of the delivery conduits 12 ahead of the stream select valve 15. Also, as described earlier, steam, or some other suitable purge fluid is directed into each of the conduits 17 through a line 18. And each of the backflush valves 19 is used to backflush the purge fluid through conduit 12 and back into the process apparatus (reactor 10).

The sampling system of this invention also includes a by-pass conduit 20, with a by-pass valve 21 installed in the conduit. At one end the conduit 20 is connected into the delivery conduit 12 ahead of the analyzer 11. At the opposite end the conduit 20 is connected into a discharge conduit 22 behind the analyzer (that is, on the downstream side of the analyzer). During a sampling operation a conventional timing sequence module (not shown) automatically controls the opening and closing of each of the stream select valves 15, the backflush valves 19 and the by-pass valve 21. The timing module can also automatically control a sample injection valve (not shown), which may be associated with the analyzer 11.

Referring to a given sampling sequence, the timing module will actuate (open) one of the stream select valves 15, and it will deactivate (close) the remaining stream select valves. Simultaneously, the timing module will actuate (open) each of the backflush valves 19 (which are associated with the deactivated stream select valves). This permits a continuous flow of the sample component, at all times, through a delivery conduit 12 into the analyzer 11. At the same time, there is a continuous flow of the purge fluid (such as steam) back into the chemical process apparatus (reactor 10) through each of the remaining delivery conduits 12.

As each delivery conduit 12 is switched from the purge sequence back to the sample flow sequence, the sample conponent flowing toward analyzer 11 will contain a small amount of the purge fluid (steam). The purge fluid thus represents a "contaminant" portion which is detrimental to a true analysis of the sample component. This problem is overcome by diverting the "contaminated" sample flow through the by-pass conduit 20 and into the discharge conduit 22. After a very short period, of a relatively rapid flow of the sample component through the by-pass conduit 20, the sample will clear itself of the purge fluid. When the sample is again clear, the timing module closes valve 21, so that the flow of sample to analyzer 11 is resumed.

In some sampling operations the desired procedure may call for carrying the vapor phase sample directly from the analyzer 11 to a suitable disposable point, such as an incinerator. In other operations, as mentioned earlier, the vapor phase sample may contain a mixture of condensable and non-condensable components at ambient temperature and pressure. Where the sample contains condensable components, it may make the process more economical to condense these components to a liquid phase, after analysis, and then recycle the liquid back into the chemical process.

In the first operation described above, the vapor phase sample is discharged from the analyzer 11 and carried through conduit 22 directly to the desired disposal point. For the second operation described above (the sample contains condensable components), the vapor phase sample is carried by conduit 22 into a suitable condenser means, such as a shell and tube heat exchanger 23. In heat exchanger 23 the vapor phase sample stream is cooled to near ambient temperature and the condensed liquid drops through a drain line 24 and into a collecting vessel 25 (holding pot). During the cooling step the non-condensable components will remain in the vessel 25 as a vapor phase. A purge fluid, such as nitrogen, is then used to sweep the non-condensable gases out of vessel 25 through a vent line 26.

A conventional liquid level sensor 27 is associated with collecting vessel 25 to control the height of liquid in this vessel. In addition, sensor 27 is electrically connected to a control device 28, which has a high/low set point. The control 28 is, in turn, connected into a pump 29. When the liquid in vessel 25 rises above the high set point, control 28 turns on pump 29. The pump takes the liquid down to the low set point and then shuts off. The liquid which is discharged from the pump is carried out through an outlet line 30 which carries it back to a suitable return point in the chemical process.

Various operating conditions and structural details of this invention will now be discussed. It was mentioned earlier that the section of conduit 12 between shut-off valve 13 and analyzer 11 is heated to a temperature high enough to maintain the sample leaving the process (reactor 10) in a vapor state. The actual temperature at which conduit 12 is heated will vary according to the composition of the chemical sample to be analyzed, and the pressure of the system in which the chemical is being processed. For example, in one embodiment of this invention, the system described herein was used to provide a vapor phase sample, for analysis, of a production plant stream which contained a mixture of water, hydrogen, oxides of carbon, aromatic hydrocarbons, and aliphatic hydrocarbons. At ambient temperature and pressure this mixture comprises three distinct phases: a non-condensable gas phase, an aqueous phase, and an organic liquid phase.

The non-condensable gas phase is made up of the hydrogen and oxides of carbon. The aqueous phase comprises the water and some of the aromatic hydrocarbons which dissolve in the water. The organic liquid phase includes some of the water, and the mixture of the aromatic and aliphatic hydrocarbons. To maintain this mixture as a vapor phase, for sampling, the delivery conduit 12 was maintained at a temperature of about 200° C. After the vapor phase sample was analyzed the vapor phase was condensed to a liquid according to the procedure described earlier. The liquid phase components were then recycled back into the production process and the non-condensable gases were vented to the atmosphere from the collecting vessel 25.

In the practice of this invention the analyzer means 11 can be any of the conventional on-line analyzers capable of performing a vapor phase analysis. Typical of such analyzer instruments are gas chromomatographs, mass spectrometers, and infrared or ultraviolet analyzing instruments. The shut-off valve 13 is typically a gate valve or other suitable conventional valve designed for high temperature service. Filter 14 can be any of various commercially available in-line filter devices capable of removing particulate matter from a vapor phase sample. The stream select valves 15 and backflush valves 19 are conventional bellows valves designed for high temperature service. A conventional ball valve of the type generally used with a gas chromomatagraph is suitable for the by-pass valve 21.

The invention claimed is:

1. A system for providing a vapor phase chemical sample for analysis, said vapor phase sample containing components which are condensable, and components which are non-condensable, at atmospheric pressure and at ambient temperature; the system comprising:

a chemical analyzer means, adapted for receiving and analyzing said vapor phase sample;

at least one delivery conduit which connects the analyzer means to at least one chemical process apparatus, for delivering the vapor phase sample to the analyzer;

a heater means associated with each delivery conduit, for heating the delivery conduit to a temperature sufficient to maintain the sample in a vapor phase;

a shut-off valve, and a stream select valve, each valve being installed in the delivery conduit between the chemical process apparatus and the analyzer means, the stream select valve being adapted for selecting a specific portion of the vapor phase sample for delivery to the analyzer means;

a purge conduit connected into each delivery conduit ahead of the stream select valve and behind the shut-off valve, for receiving and carrying a purge fluid into said delivery conduit;

a backflush valve which is installed in each purge conduit, and which is adapted for backflushing the purge fluid through each delivery conduit and back into the chemical process apparatus;

a discharge conduit connecting the analyzer means to a disposal point, for carrying the vapor phase sample out of the analyzer means;

a by-pass conduit which connects into the delivery conduit ahead of the analyzer and into the discharge conduit behind the analyzer, for carrying a contaminated portion of the vapor phase sample past the analyzer means; and a by-pass valve installed in the by-pass conduit, for regulating flow of the contaminated sample through the by-pass conduit;

a condenser means connected into the discharge conduit, for converting the condensable vapor phase components to a liquid phase component;

a collecting vessel, for collecting the liquid phase component, and the non-condensable vapor phase component;

pump means connected into the collecting vessel and in communication with the chemical process apparatus, for pumping the liquid phase component back to said chemical process apparatus;

control means associated with the collecting vessel and the pump means, for regulating the liquid level in said collecting vessel; and vent means in the collecting vessel, for carrying the non-condensable vapor phase components out of the collecting vessel.

2. The system of claim 1 which further includes a plurality of delivery conduits, each of said conduits connecting the analyzer to a chemical process apparatus.

3. The system of claim 1 which further includes a filter means located in the delivery conduit ahead of the stream select valve, for removing particulate matter from the vapor phase sample.

4. The system of claim 1 in which the heater means is a steam trace line attached to the delivery conduit.

5. The system of claim 1 in which the chemical analyzer means is a gas chromatograph.

* * * * *